United States Patent [19]

King

[11] Patent Number: 4,897,788
[45] Date of Patent: Jan. 30, 1990

[54] IMAGE CORRECTION FOR COMPUTED TOMOGRAPHY TO REMOVE CROSSTALK ARTIFACTS

[75] Inventor: Kevin F. King, New Berlin, Wis.

[73] Assignee: General Electric Company, Milwaukee, Wis.

[21] Appl. No.: 182,591

[22] Filed: Apr. 18, 1988

[51] Int. Cl.⁴ .......................... A61B 6/02; G01N 23/02
[52] U.S. Cl. ................................................. 364/413.15
[58] Field of Search ........................ 378/4, 12, 901, 19; 364/413.14, 413.15, 413.16, 413.19

[56] References Cited

U.S. PATENT DOCUMENTS 4,670,840  6/1987  Freundlich ...................... 364/413.19

OTHER PUBLICATIONS

Rawlins, T. G. R. et al., "Microprocessor Crosstalk Correction in Multiple-Detector Gamma Counters", Phys. Med. & Biol. (GB), vol. 26, No. 3, May 1981, 425-34.

Primary Examiner—Clark A. Jablon
Attorney, Agent, or Firm—James O. Skarsten; Douglas E. Stoner

[57] ABSTRACT

A correction method and apparatus for Computed Tomography (CT) removes ring and streak artifacts from images by correcting for data contamination by crosstalk errors. Crosstalk coupling between all adjacent detectors can be measured using an off-center phantom to provide X-ray flux having a changing gradient profile from view to view across the detector array of the CT apparatus. Correction factors are found that will remove crosstalk contamination from subsequently measured imaging data.

17 Claims, 1 Drawing Sheet

IMAGE CORRECTION FOR COMPUTED TOMOGRAPHY TO REMOVE CROSSTALK ARTIFACTS

BACKGROUND OF THE INVENTION

The present invention relates in general to generation of images using x-ray computed tomography (CT) apparatus, and more specifically to correction of x-ray measurements contaminated by crosstalk errors between adjacent detectors in the CT apparatus.

Modern CT equipment reconstructs cross-sectional images of the x-ray attenuation coefficient in a subject using a rotating source of fan-beam x-rays and an array of x-ray detectors for measuring the fan beam after attenuation by the subject at a plurality of rotational positions (i.e., views). In the third-generation CT scanner, a rotating detector array comprises many detector elements (or channels) in side-by-side alignment in the plane of rotation on the opposite side of the subject from the fan-beam source. The x-ray measurements obtained by each of the detector elements in each of the views are combined to form an image using a well-known method, such as filtered back projection.

Since the elements in a detector array must be closely spaced, they are likely to be subject to crosstalk, where x-rays impinging on one channel create output signals in that channel and in adjacent channels. In commonly used xenon-gas detectors, crosstalk is caused by x-ray scatter between detector cells and by leakage of charge between cells. In solid-state detectors, crosstalk is caused by x-ray scatter, leakage of visible light produced in one scintillator into the photosensitive diode associated with a different scintillator, and leakage of electrical signals between adjacent diodes.

Crosstalk creates ring and streak artifacts in reconstructed images from third generation CT scanners because of the distortions in the individual x-ray measurements of each channel. As the name suggests, the ring artifacts appear as bright or dark circles or portions of circles centered on the rotation axis (i.e., isocenter) of the source and detector array. The rings tend to appear near the center of the field of view and in areas of abrupt change in attenuation coefficient. Streak artifacts appear as bright or dark lines tangential to the edges of dense (i.e., high x-ray attenuating) objects.

Previous efforts to reduce ring and streak artifacts include the use of matched detectors having a high degree of uniformity between elements. If crosstalk characteristics for all adjacent channels are substantially equal, then accumulated crosstalk errors in each channel will approximately cancel since x-ray intensity variation across the detectors during a view is approximately piecewise linear. However, matched detector arrays are difficult to implement and are expensive.

Another approach has been to inspect a reconstructed image for ring artifacts and manipulate the image in an attempt to remove the rings using numerical methods. However, this approach cannot remove streak artifacts. Furthermore, ring artifacts beyond a certain severity cannot be removed.

Accordingly, it is a principal object of the present invention to reduce crosstalk artifacts in CT images without the use of special matched detectors.

It is another object to provide a method and apparatus to reduce all artifacts in CT images caused by crosstalk, including ring artifacts and streak artifacts.

It is a further object to characterize the crosstalk of a detector array in a simple and convenient manner, without special preparation or hardware.

It is another object to remove crosstalk errors from CT data prior to image reconstruction.

SUMMARY OF THE INVENTION

These and other objects are achieved by a method and apparatus for correcting individual x-ray measurements obtained from an array of detectors in each view of a CT scan so as to reduce crosstalk artifacts in an image reconstructed from the measurements. The method comprises the steps of (1) obtaining a plurality of x-ray measurements from the outputs of the detectors during the view, which measurements are contaminated by crosstalk errors arising between adjacent detectors, and (2) determining a corrected measurement from each respective x-ray measurement from a respective detector by summing therewith at least a portion of at least one adjacent x-ray measurement in the view from an adjacent detector multiplied by a crosstalk correction factor dependent on the crosstalk coupling of the respective detector with each of its adjacent detectors.

In another aspect of the invention, a method is provided for finding correction factors to calibrate a plurality of output signals from a plurality of x-ray detectors in a CT scanner comprising the steps of (1) radiating x-ray energy from the x-ray source toward the detectors in each of a plurality of views such that the energy arriving at the detectors in each respective view has a respective profile, (2) measuring the output from each detector in each view, and (3) determining the correction factors for each respective detector based on the variation of its output signals for each of the views.

BRIEF DESCRIPTION OF THE DRAWINGS

The novel features of the invention are set forth with particularity in the appended claims. The invention itself, however, both as to its organization and method of operation, together with further objects and advantages thereof, may best be understood by reference to the following description taken in conjunction with the accompanying drawings in which:

DETAILED DESCRIPTION OF PREFERRED EMBODIMENTS

Figure 1:
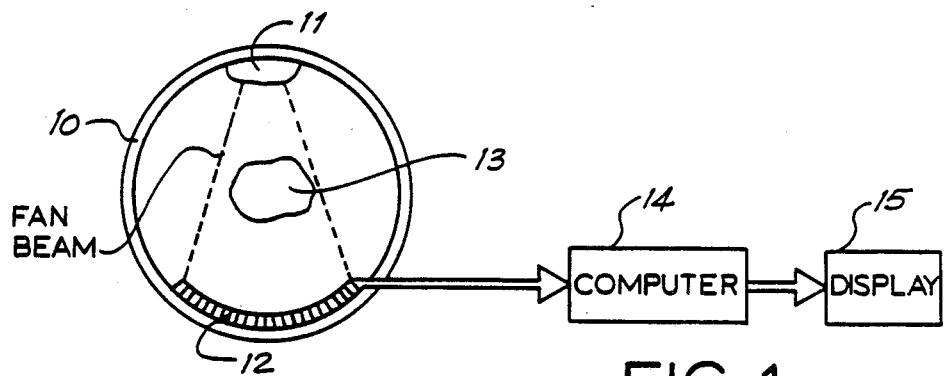
FIG. 1 is a diagram of portions of a computed tomography data acquisition system and data processing and display apparatus.

Referring now to FIG. 1, a computed tomography scanner includes a data acquisition system having a rotating gantry 10 which carries a fan-beam x-ray source 11 and a detector array 12 on opposite sides of gantry 10. An object 13 to be imaged is located within gantry 10 such that it can be irradiated by x-rays for a plurality of different views, each view being at a different rotational position of gantry 10. The x-ray attenuation data measured by detector array 12 for each view is provided to an image processing section including a computer 14 which performs any corrections on the data and reconstructs a cross-sectional image of object 13 using any well-known reconstruction technique such as filtered back-projection. The reconstructed image is provided from computer 14 to a display 15 such as a CRT or a filming device.

Figure 2:
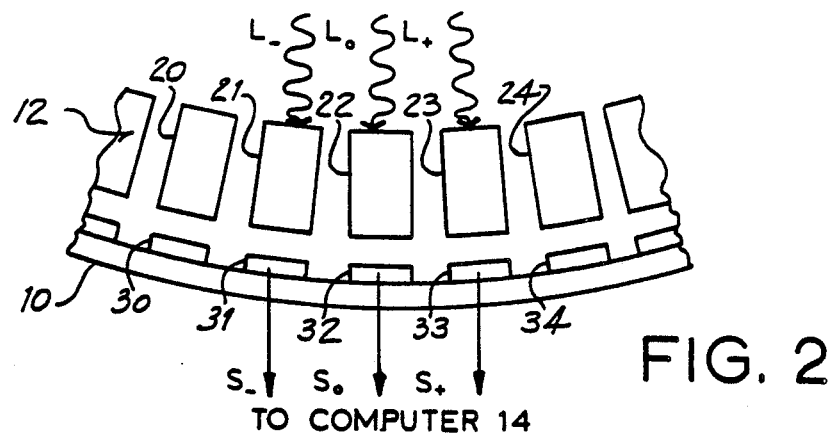
FIG. 2 is a cross-sectional representation of some of the components of a detector array.

FIG. 2 shows a portion of a preferred embodiment of detector array 12 in greater detail. This embodiment includes solid-state detector elements, but the crosstalk model and inventive image correction techniques described below are equally applicable to other detectors, such as xenon-gas detectors.

A plurality of solid-state scintillators 20-24 and their respective photosensitive diodes 30-34 are secured to gantry 10 by supporting and separating means (not shown). Each scintillator is typically comprised of a crystal, such as sodium iodide, which can absorb an x-ray photon and, in response, emit a visible light photon. The visible light photons interact with the photosensitive diodes which provide an electrical signal which is a measure of the x-ray flux irradiating each respective detector.

A model for the relative output signal contributions for each respective detector element will be described with reference to the detector element comprising scintillator 22 and diode 32. That particular element directly receives an x-ray flux $L_o$ and has an electrical output signal $S_o$. One adjacent element receives a flux input $L_-$ and has an output signal $S_-$ while the other adjacent element receives a flux input $L_+$ and has an output signal $S_+$.

Output signal $S_o$ is contaminated by crosstalk leakage. To a very good approximation, crosstalk leakage only occurs between adjacent elements. Therefore, the contaminating signals in any given element only occur as a result of signals from channels on either side.

Based on the model of FIG. 2, the output signal $S_o$ from a given element can be approximated by $$S_o = \epsilon_- L_- + \epsilon_o L_o + \epsilon_+ L_+, \quad (1)$$

where $\epsilon_o$ is the electrical gain of the given element and $\epsilon_-$ and $\epsilon_+$ are the crosstalk coupling strengths between the given element and the two adjacent elements, respectively. The effects of crosstalk are removed, in the present invention, by subtracting out the contaminating portions of each output signal once the crosstalk coupling strengths $\epsilon_+$ and $\epsilon_-$ are determined.

Let $S_-$, $S_o$ and $S_+$ be reference normalized output signals from three adjacent detectors as shown in FIG. 2. The corrected measurement $S'$ for each flux measurement in each view will estimate the value of $\epsilon_o L_o$. According to the model of the present invention, we have $$S' = S_o - \epsilon_- L_- - \epsilon_+ L_+. \quad (2)$$

However, the values for $L_-$ and $L_+$ are unknown and must be estimated. For the adjacent detectors, the output signals neglecting crosstalk are $$S_- = \epsilon_{o-} L_- \text{ and}$$

$$S_+ = \epsilon_{o+} L_+$$

where $\epsilon_{o-}$ and $\epsilon_{o+}$ are the electrical gain of each adjacent detector, respectively. Since crosstalk errors have experimentally been found to be typically less than 10%, these equalities can be substituted into Equation (2) with little error as follows:

$$S' = S_o - (\epsilon_-/\epsilon_{o-})S_- - (\epsilon_+/\epsilon_{o+})S_+. \quad (3)$$

The detectors are designed so that the electrical gains of all detectors are substantially the same. Further substitution of $\epsilon_{o-} = \epsilon_o$ and $\epsilon_{o+} = \epsilon_o$ gives $$S' = S_o - (\epsilon_-/\epsilon_o)S_- - (\epsilon_+/\epsilon_o)S_+. \quad (4)$$

Application of Equation (4) to each of the measurement values in each of the views of a CT scan has provided image data that upon reconstruction gives images with significantly reduced crosstalk artifacts.

When using Equation (4) to generate corrected measurements, $\epsilon_+$ and $\epsilon_-$ can be found empirically (e.g., estimated based on the detector structure) or by direct or indirect measurement. One measurement technique is to irradiate the detector array with x-rays while slowly passing a slitted lead plate over the array. The width of the slit must be narrow enough to only irradiate one element at a time. As each detector element is irradiated, the output signals of the adjacent elements are measured and normalized by the output signal of the irradiated element. This gives $\epsilon_-/\epsilon_{o-}$ and $\epsilon_+/\epsilon_{o+}$ rather than $\epsilon_-/\epsilon_o$ and $\epsilon_+/\epsilon_o$, but the differences in detector electrical gain is typically negligible.

The lead slit test and other similar detector characterizations have the drawback that they can only be done using specialized equipment which adds complications and expense. Therefore, a test which can be performed after a scanner is installed, without special equipment, is desirable.

According to a further improvement of the invention, crosstalk is characterized according to the difference in crosstalk coupling of each detector to its adjacent detectors (e.g., $\epsilon_+ - \epsilon_-$). This characterization cn also be used to remove both ring artifacts and streak artifacts by means of several methods presented below. These methods can be implemented in conjunction with an inventive technique for measuring crosstalk coupling differences, also presented below.

Letting $\epsilon = (\epsilon_- + \epsilon_+)/2$ be the average crosstalk coupling and $\delta = \epsilon_+ - \epsilon_-$ be the difference in crosstalk coupling, gives $$\epsilon_+ = \epsilon + \delta/2 \text{ and}$$

$$\epsilon_- = \epsilon - \delta/2.$$

Inserting these expressions into Equation (1) results in $$S_o = \epsilon_o L_o + \epsilon(L_+ + L_-) + \delta(L_+ - L_-)/2. \quad (5)$$

Using further rearrangement and defining $D_1$ and $D_2$ as discrete approximations to the average first and second derivatives, respectively, of the flux intensity variations between elements, where $$D_1 = (L_+ - L_-)/2 \text{ and}$$

$$D_2 = L_+ + L_- - 2L_o,$$

gives $$S_o = (\epsilon_o + 2\epsilon)L_o + \epsilon D_2 + \delta D_1. \quad (6)$$

This equation shows that the difference in crosstalk between the channels on either side of a given element couples to the first derivative of the x-ray flux while the average crosstalk of those two channels couples to the second derivative of the x-ray flux and also contributes to the apparent gain of the element (i.e., multiplies the x-ray flux $L_o$). The apparent gain contribution due to the average crosstalk will be divided out when the data is normalized by the standard air calibration scan.

For x-ray signals attenuated by most objects, the second derivative term $D_2$ has been found to be negligible compared to the other terms, except possibly very near the edge of a highly attenuating object.

From the foregoing, it is clear that almost all of the crosstalk artifact is due to the difference in crosstalk $\delta$ between the channels on either side of the given element. This contribution is significant only when an x-ray flux gradient exists across the detectors.

Since ring and streak artifacts are almost completely due to the crosstalk difference $\delta$, it is possible to perform the correction by using only this difference instead of $\epsilon_+$ and $\epsilon_-$. Thus, each flux measurement can be corrected (dropping the negligible terms involving $D_2$ from Equation (6)) using the equation $$S' = S_o - \delta D_1 = S_o - (\delta/2\epsilon_o)S_+ + (\delta/2\epsilon_o) S_-. \quad (7)$$

Experiment has shown Equations (4) and (7) to give identical crosstalk artifact removal.

A further simplification can be achieved by rearranging the equation for $D_2$:

$$L_- = D_2 - L_+ + 2L_o$$

and substituting into Equation (1) to give $$S' = (\epsilon_o + 2\epsilon_-) L_o + \epsilon_- D_2 + \delta L_+.$$

Again, the second derivative term involving $D_2$ is negligible and the $\epsilon_-$ term mostly contributes to an apparent gain shift of the detector which will drop out later after dividing by the air calibration scan. Therefore, the crosstalk correction can be performed with the simplified formula:

$$S' = S_o - (\delta/\epsilon_o)S_+. \quad (8)$$

A different simplification can be achieved by rearranging the equation for $D_2$:

$$L_+ = D_2 - L_- + 2L_o$$

and substituting into Equation (1) to give $$S' = (\epsilon_o + 2\epsilon_+)L_o + \epsilon_+ D_2 - \delta L_-.$$

Again, the second derivative term involving $D_2$ is negligible and the $\epsilon_+$ term mostly contributes to an apparent gain shift of the detector which will drop out after dividing by the air calibration scan. The crosstalk correction can be performed with the alternative simplified formula $$S' = S_o + (\delta/\epsilon_o)S_-. \quad (8')$$

Of the correction methods described (i.e., Equations (4), (7) (8) and (8')), all give comparable correction of ring and streak artifacts due to crosstalk but Equations (8) and (8') are the most efficient to implement because they require only one multiply/add rather than two and because they use the easily obtained crosstalk difference $\delta$ rather than actual coupling values $\epsilon_+$ and $\epsilon_-$.

In a preferred embodiment of the invention, the difference $\delta$ in crosstalk coupling strength to the two adjacent detectors of each respective detector is measured by systematically varying the x-ray flux intensity difference provided to the adjacent detectors, thus varying the crosstalk contamination received by each respective detector in a predetermined way. Each view of a crosstalk calibration scan has x-ray flux radiated onto the detector array with a respective energy profile. The detector outputs are measured and crosstalk correction factors are determined for each detector based on the variation of its output signal from each of the views.

It was discussed earlier that an x-ray signal gradient is necessary to produce crosstalk artifacts. Scanning of phantoms produces large gradients near their edges, which is why they exhibit crosstalk artifacts there. For the elements shadowed by the center of such a phantom, there is almost no signal gradient. If the phantom were placed off center, its shadow would move across the detector array during the course of an axial scan so that the center elements would experience varying degrees of crosstalk as they were shadowed by the various parts of the phantom. For example, consider the effect on the center detector channel during a 360° axial scan. With the phantom placed above isocenter, the channel is first shadowed by the phantom center, by one edge, then by the center again, by the other edge, and finally by the center. Thus, an off-center, round phantom can conveniently be used to generate the needed varying gradient profiles. From the x-ray measurements obtained from each respective detector element for all views, a least squares fit of the crosstalk error to the magnitude of the varying gradient at the respective element yields an estimate of $\delta$ for that element. The values for $\delta$ may be used in Equations (7) (8) or (8') to correct raw measurements and reduce crosstalk artifacts in subsequently reconstructed images.

Figure 3:
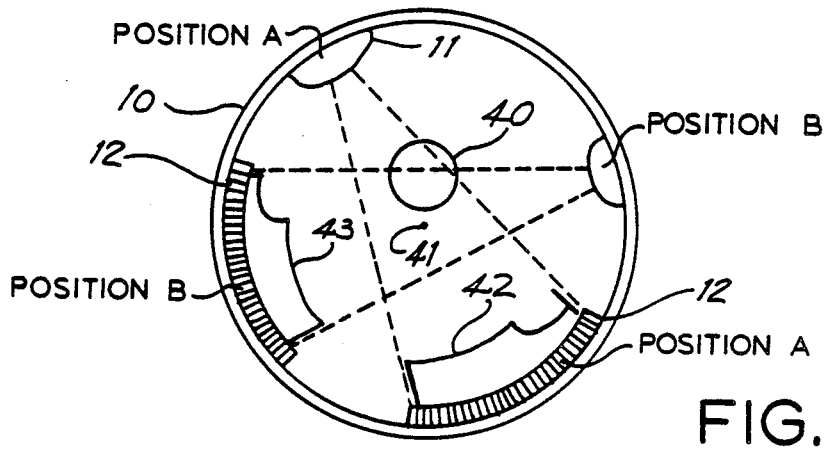
FIG. 3 shows the derivation of various x-ray flux profiles obtained with an off-center phantom.

FIG. 3 shows a round, smooth phantom 40 offset from isocenter 41 of a CT scanner. With source 11 and detector array 12 in position A, detector array 12 receives an x-ray energy intensity profile 42. In the view corresponding to the rotation of gantry 10 to position B, a profile 43 is received by array 12. A typical scan comprises about one thousand views. Although the off-center phantom will thus provide about one thousand different profiles, crosstalk characterization can be done with fewer views.

Prior to conducting a crosstalk calibration scan with an off-center phantom, it is necessary to perform an air calibration scan to normalize all measurements for variations in gain between detector elements. In an air calibration scan, source 11 irradiates all elements in detector array 12 equally. Any other known errors in the x-ray measurements relating to the specific apparatus being used should be corrected or compensated for by using various known techniques prior to performing the crosstalk calculations in order to obtain the most accurate crosstalk correction.

Since each view of a scan is an independent measurement of the crosstalk, quantum noise is a problem. If quantum noise is not suppressed, it can exceed the crosstalk errors so that spurious results will be obtained. To overcome this problem, x-ray flux can be increased. This can be accomplished with multiple scans of the phantom with measurements from corresponding views being added together.

A preferred embodiment of phantom 40 is a small (e.g., about 5 inch diameter) disk made of a homogeneous material with low x-ray attenuation such as polyvinylchloride (PVC) or other thermoplastic resin. The small size of the phantom is preferred because it provides a large x-ray gradient for areas shadowed by its edges. The sides of the phantom are smooth in order to avoid any disruption in the profiles which could cause errors in the crosstalk characterization.

The crosstalk difference $\delta$ (or more specifically the term $\delta/\epsilon_o$) can be calculated as follows: Let the output for a particular detector for the air calibration, corrected for variations in the x-ray flux and for offsets in the data acquisition system, be given by $C_o$:

$$C_o = (\epsilon_o + 2\epsilon)A_o + (\delta/2)(A_+ - A_-) \quad (9)$$

where $A_o$, $A_+$ and $A_-$ represent the view averaged x-ray flux impinging on three adjacent elements during the air calibration scan (neglecting the second derivative term). A corresponding detector output for one view of the phantom is given by $$S_o = (\epsilon_o + 2\epsilon)L_o + (\delta/2)(L_+ - L_-). \quad (10)$$

The air calibrated phantom measurement is obtained by dividing Equation (10) by Equation (9):

$$S_o/C_o = \frac{(\epsilon_o + 2\epsilon)L_o + (\delta/2)(L_+ - L_-)}{(\epsilon_o + 2\epsilon)A_o + (\delta/2)(A_+ - A_-)}. \quad (11)$$

Since $A_o$, $A_+$ and $A_-$ are approximately equal (i.e., $A_+ - A_- \approx 0$), and since $\epsilon_o >> 68$, Equation (11) can be approximated by $$S_o/C_o = L_o/A_o + (\delta/2\epsilon_o)(L_+/A_+ - L_-/A_-). \quad (12)$$

Taking the negative log and using that fact that $\delta/\epsilon_o << 1$ gives $$-\ln(S_o/C_o) = -\ln(L_o/A_o) + \quad (13)$$

$$(\delta/2\epsilon_o)(A_o/L_o)(L_-/A_- - L_+/A_+).$$

The left-hand side of Equation (13) can be calculated directly from the phantom measurement obtained as a result of Equation (11). Let $X = -\ln(S_o/S_c)$. Note that the terms $\epsilon_+$ and $\epsilon_-$ vary greatly among elements in the array, so that crosstalk contamination also varies greatly across the array (i.e., varies according to a high frequency). Then the first term on the right-hand side can be approximated by a suitable low pass filtering of X:

$$Y = -\ln(L_o/A_o) = S*X,$$

where $S*X$ represents convolution by an appropriate low pass filter. The terms $L_o/A_o$, $L_-/A_-$ and $L_+/A_+$ can be calculated using $$L_o/A_o = \exp(-Y),$$

and shifting this result by one channel to get $L_-/A_-$ or $L_+/A_+$. The term $\delta/\epsilon_o$ can then be calculated by doing a least squares fit over all views for each detector element.

For each view, the low pass filter will give spurious results for Y as it encounters the edge of the phantom. To avoid this problem, values near the edge of the phantom are replaced with zeroes. For the elements near the edge of the phantom for that particular view, no data is therefore added to the least squares fit sums. All signals outside the phantom edge are also zeroed since crosstalk values could not be measured for them on that particular view.

To find the least squares fit values, let $$Z = (1/2)(A_o/L_o)(L_-/A_- - L_+/A_+). \quad (14)$$

Then Equation (13) can be written $$X - Y = (\delta/\epsilon_o)Z \quad (15)$$

The least square fit value for $\delta/\epsilon_o$ is then given by $$\delta/\epsilon_o = \Sigma(X - Y)Z/\Sigma Z^2, \quad (16)$$

where the value is calculated for each detector channel of interest and the sum is taken over all views in the scans. If multiple scans are used, the sums are accumulated over all of the scans.

While preferred embodiments of the invention have been shown and described herein, it will be understood that such embodiments are provided by way of example only. Numerous variations, changes and substitutions will occur to those skilled in the art without departing from the spirit of the invention. Accordingly, it is intended that the appended claims cover all such variations as fall within the spirit and scope of the invention.

What is claimed is:

1. A method for correcting individual flux measurements obtained from an array of detectors in a view of a Computed Tomography (CT) scan so as to reduce crosstalk artifacts in an image reconstructed from said measurements, said method comprising the steps of:

obtaining a plurality of x-ray measurements from the outputs of said detectors during said view, said measurements being contaminated by crosstalk errors arising between adjacent detectors; and determining a corrected measurement from each respective x-ray measurement from a respective detector by summing therewith at least a portion of at least one adjacent x-ray measurement in said view from an adjacent detector multiplied by a crosstalk correction factor dependent on the crosstalk coupling of said respective detector with each of its adjacent detectors.

2. The method of claim 1 wherein said corrected measurement is obtained according to the formula $$S' = S_o - (\epsilon_-/\epsilon_o)S_- - (\epsilon_+/\epsilon_o)S_+$$

where $S'$ is the corrected measurement, $S_o$ is the measurement from a respective detector which is to be corrected, $S_+$ is the measurement from one adjacent detector, $S_-$ is the measurement from the other adjacent detector, $\epsilon_o$ is the signal gain of said respective detector, $\epsilon_+$ is the crosstalk coupling strength between said respective detector and said one adjacent detector and $\epsilon_-$ is the crosstalk coupling strength between said respective detector and said other adjacent detector.

3. The method of claim 1 wherein said corrected measurement is obtained according to the formula $$S' = S_o - (\delta/2\epsilon_o)S_+ + (\delta/2\epsilon_o)S_-$$

where $S'$ is the corrected measurement, $S_o$ is the measurement from a respective detector which is to be corrected, $S_+$ is the measurement from one adjacent detector, $S_-$ is the measurement from the other adjacent detector, $\epsilon_o$ is the signal gain of said respective detector and $\delta$ is the difference in crosstalk coupling strength between said respective detector and each of said adjacent detectors.

4. The method of claim 1 wherein said corrected measurement is obtained according to the formula $$S' = S_o - (\delta/\epsilon_o)S_+$$

where $S'$ is the corrected measurement, $S_o$ is the measurement from a respective detector which is to be corrected, $S_+$ is the measurement from one adjacent detector, $\epsilon_o$ is the signal gain of said respective detector and $\delta$ is the difference in crosstalk coupling strength between said respective detector and each of its adjacent detectors.

5. The method of claim 1 wherein said corrected measurement is obtained according to the formula $$S' = S_o + (\delta/\epsilon_o)S_-$$

where $S'$ is the corrected measurement, $S_o$ is the measurement from a respective detector which is to be corrected, $S_-$ is the measurement from one adjacent detector, $\epsilon_o$ is the signal gain of said respective detector and $\delta$ is the difference in crosstalk coupling strength between said respective detector and each of its adjacent detectors.

6. A method of finding correction factors to calibrate a plurality of output signals from a plurality of X-ray detectors in a CT scanner, said scanner including a source of X-rays, said method comprising the steps of:
radiating X-ray energy from said source toward said detectors in each of a plurality of views such that the energy arriving at said detectors in each respective view has a respective profile;
measuring the output signal from each of said detectors for each of said views; and
determining said correction factors for each respective detector based on the variation of its output signals from each of said views.

7. The method of claim 6 wherein said radiating step includes the step of placing a smooth phantom at an off-center location in said CT scanner to provide said respective profiles for said views.

8. The method of claim 6 wherein said radiating and measuring steps are performed a plurality of times and the results combined in order to reduce the effects of quantum noise.

9. The method of claim 6 further comprising the step of:
conducting an air calibration scan prior to said radiating step to provide an averaged reference output signal for each respective detector.

10. The method of claim 9 wherein each of said correction factors corresponding to a respective detector is proportional to $\delta$, the difference in crosstalk coupling to both adjacent detectors of each respective detector, and wherein said correction factor determination comprises the step of:
evaluating $S \approx C$ to find $\delta$ for each respective detector, where $S$ is the respective measured output signal and $C$ is the respective reference output signal for a respective detector.

11. The method of claim 10 wherein $S \approx C$ is evaluted for each detector o using the equation $$S_o/C_o + L_o/A_o + (\delta/2\epsilon_o)(L_+/A_+ - L_-/A_-)$$

where $L_o$, $L_+$ and $L_-$ are the actual x-ray flux radiated during a respective view onto said detector o, one adjacent detector and the other adjacent detector, respectively, $A_o$, $A_+$ and $A_-$ are the averaged X-ray flux radiated during said air calibration scan onto said detector o, said one adjacent detector and said other adjacent detector, respectively, and where $\epsilon_o$ is the signal gain of each respective detector o.

12. The method of claim 11 wherein the term $L_o/A_o$ for each respective detector is approximated by low-pass filtering of $S_o/C_o$.

13. The method of claim 11 wherein the term $\delta/\epsilon_o$ is calculated for each detector using a least-squares fit over said plurality of views.

14. Computed tomography apparatus comprising:
an X-ray source;
an array of X-ray detectors, each detector producing an output signal in response to X-rays radiated from said source, said array and said source being adapted for rotation about a central volume to generate a plurality of views;
measurement means coupled to said array for obtaining x-ray measurements from said detectors; and
correction means coupled to said measurement means for determining a corrected measurement for a respective x-ray measurement from a respective detector by summing therewith at least a portion of at least one adjacent x-ray measurement in the same view from an adjacent detector multiplied by a crosstalk correction factor dependent on crosstalk coupling of said respective detector with each of its adjacent detectors.

15. The apparatus of claim 14 further comprising:
image reconstruction means coupled to said correction means for reconstructing a CT image from said corrected measurements;
whereby said reconstructed image has significantly reduced ring and streak artifacts resulting from crosstalk errors.

16. The apparatus of claim 14 further comprising:
factor means coupled to said measurement means and to said correction means for determining said correction factors from x-ray measurements during a multiple-view calibration procedure and providing said correction factors to said correction means, said factor means being responsive to a gradient profile of each respective view in said calibration procedure.

17. The apparatus of claim 16 further comprising:
locating means for locating an X-ray phantom in said central volume with an off-center location, so as to generate said gradient profiles.

* * * * *